United States Patent [19]

Duffett

[11] Patent Number: Plant 5,738

[45] Date of Patent: May 6, 1986

[54] CHRYSANTHEMUM PLANT NAMED RAVE

[75] Inventor: William E. Duffett, Salinas, Calif.

[73] Assignee: Yoder Brothers, Inc., Barberton, Ohio

[21] Appl. No.: 644,267

[22] Filed: Aug. 27, 1984

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Evans

[57] ABSTRACT

A chrysanthemum plant named Rave characterized as to uniqueness by the combined characteristics of flat capitulum form, anemone capitulum type with 3 cm. cushion, purple-violet ray floret color, diameter across face of capitulum ranging from 5 to 6 cm. at maturity, uniform seven to eight week flowering response, medium plant height, semi-spreading branching pattern, and tolerance of both low winter 13° C. minimum and high summer 24° C. night to 38° C. day temperatures for bud initiation and flower development.

3 Drawing Figures

The present invention comprises a new and distinct cultivar of *Chrysanthemum morifolium,* Ramat., named Rave.

Rave is a product of a planned breeding program which had the objective of creating new chrysanthemum cultivars for pinched spray pot mum programs having anemone capitulum type, purple floret color, eight week flowering response, and the ability to produce commercially acceptable quality in year round programs. Such traits in combination were not present or required improvements in previously available commercial cultivars.

Rave was originated from a cross made in a controlled breeding program in Salinas, Calif. in 1980. The female parent was Russet, disclosed in U.S. Plant Pat. No. 5,107 and originated by the present inventor from a cross between an unnamed yellow anemone and a mutant clone from Fiesta (U.S. Plant Pat. No. 3,632). The male parent of Rave was an unnamed purple daisy identified as 7828004 and originated from a cross between an unnamed seedling and Circus, disclosed in U.S. Plant Pat. No. 4,188.

Rave was discovered and selected as one flowering plant within the progeny of the stated cross by William E. Duffett in May 1981 in a controlled environment in Salinas, Calif.

The first act of asexual reproduction of Rave was accomplished when vegetative cuttings were taken from the initial selection in July, 1981 in a controlled environment in Salinas, Calif. by a technician working under formulations established and supervised by William E. Duffett. Horticultural examination of selected units initiated June 9, 1982 has demonstrated that the combination of characteristics as herein disclosed for Rave are firmly fixed and are retained through successive generations of asexual reproduction.

Rave has not been observed under all possible environmental conditions. The phenotype may vary significantly with variations in environments such as temperature, light intensity and day length. The observations, measurements and comparisons describe plants grown in Salinas, Calif. and Leamington, Ontario, Canada under greenhouse conditions which approximate those generally used in commercial practice.

The following traits have been repeatedly observed and are determined to be basic characteristics of Rave which in combination distinguish this chrysanthemum as a new and distinct cultivar;

1. Flat capitulum form.
2. Anemone capitulum type with 3 cm. cushion.
3. Purple-violet ray floret color.
4. Diameter across face of capitulum ranging from 5 to 6 cm. at maturity.
5. Uniform seven to eight week photoperiodic flowering response to short days.
6. Medium plant height (requiring 2 long day weeks prior to pinch and short days, and 1 to 2 applications of 2500 ppm B-9 SP, the first at 14, the second at 21 days after the beginning of short days to attain a flowered plant height of 25 to 35 cm. in 6" pots).
7. Semi-spreading branching pattern.
8. Tolerance of low winter 13° C. minimum temperatures.
9. Tolerance of high summer 24° C. night to 38° C. day temperatures.

The accompanying photographic drawings depict typical leaf and inflorescence characteristics of Rave. Sheet 1 is a color photograph of a plant of Rave grown as a pinched spray pot mum, with colors being as accurate as possible with renditions of this type. Sheet 2 is a black and white photograph of three views of the inflorescence of Rave. Sheet 3 shows the upper and under surface of leaves of Rave in three stages of growth (mature, intermediate, immature).

Of the many commercial cultivars known to the present inventor, the most similar in comparison to Rave is Cherub, disclosed in U.S. Plant Pat. No. 4,629. Reference is made to attached Chart A which compares certain characteristics of Rave to those same characteristics of Cherub. Traits similar in both cultivars are capitulum type, form and diameter, and branching pattern. Rave has a shorter plant height, a one to two weeks faster response time, a deeper purple ray floret color, and its tolerance of low and high temperatures results in a more extended period of value.

In the following description, color references are made to The Royal Horticultural Society Colour chart. The color values were determined between 2:45 P.M. and 3:00 P.M. on Mar. 1, 1984 under 380 foot-candle light intensity at Salinas, Calif.

Classification:

*Botanical.*—*Chrysanthemum morifolium,* Ramat., cv Rave.

*Commercial.*—Anemone spray pot mum.

I. INFLORESCENCE

A. Capitulum:

*Form.*—Flat.

*Type.*—Anemone.

*Diameter across face.*—5 to 6 cm.

B. Corolla of ray florets:

*Color (general tonality from a distance of three meters).*—Purple-violet.

*Color (upper surface).*—80B oxidizing to 80C; D.

*Color (under surface).*—82D.

*Shape.*—Oblong.

C. Corolla of disc florets:

*Color (mature).*—81C, D.

*Color (immature).*—81B, C.

D. Reproductive organs:

*Androecium.*—Present disc florets only; minimum pollen.

*Gynoecium.*—Present both ray and disc florets.

II PLANT

A. General appearance:

*Height.*—Medium.

*Branching pattern.*—Semi-spreading.

B. Foliage:

*Color (upper surface).*—137A, B.

*Color (under surface).*—147C.

*Shape.*—Deeply lobed. Blunt with moderate serration.

CHART A

COMPARISON OF RAVE AND CHERUB

| | | | | DIAMETER |
|---|---|---|---|---|
| CULTIVAR | RAY FLORET COLOR | CAPITULUM FORM AND TYPE | BRANCHING PATTERN | ACROSS FACE OF CAPITULUM |
| RAVE | PURPLE-VIOLET | FLAT ANEMONE | SEMI-SPREADING | 5 to 6 cm. |
| CHERUB | LAVENDER | FLAT ANEMONE | SEMI-SPREADING | 4.5 to 5.0 cm. |

CHART A-continued

COMPARISON OF RAVE AND CHERUB

| CULTIVAR | PLANT HEIGHT | FLOWERING RESPONSE PERIOD | TEMPERATURE TOLERANCE |
|---|---|---|---|
| RAVE | MEDIUM | SEVEN TO EIGHT WEEKS | LOW - 13° C. HIGH - 24° C. NIGHT TO 38° C. DAY |
| CHERUB | TALL | NINE WEEKS | LOW - POOR HIGH - RESPONSE SLOWED TO ELEVEN WEEKS |

COMPARISONS MADE OF PLANTS GROWN AS PINCHED SPRAY POT MUMS IN SALINAS, CALIFORNIA AND LEAMINGTON, ONTARIO, CANADA

I claim:

1. A new and distinct cultivar of *Chrysanthemum morifolium,* Ramat., plant named Rave, as described and illustrated, and particularly characterized as to uniqueness by the combined characteristics of flat capitulum form; anemone capitulum type with 3 cm. cushion purple-violet ray floret color; diameter across face of capitulum ranging from 5 to 6 cm. at maturity; uniform seven to eight week flowering response; medium plant height; semi-spreading branching pattern; and tolerance of both low winter 13° C. minimum and high summer 24° C. night to 38° C. day temperatures for bud initiation and flower development.

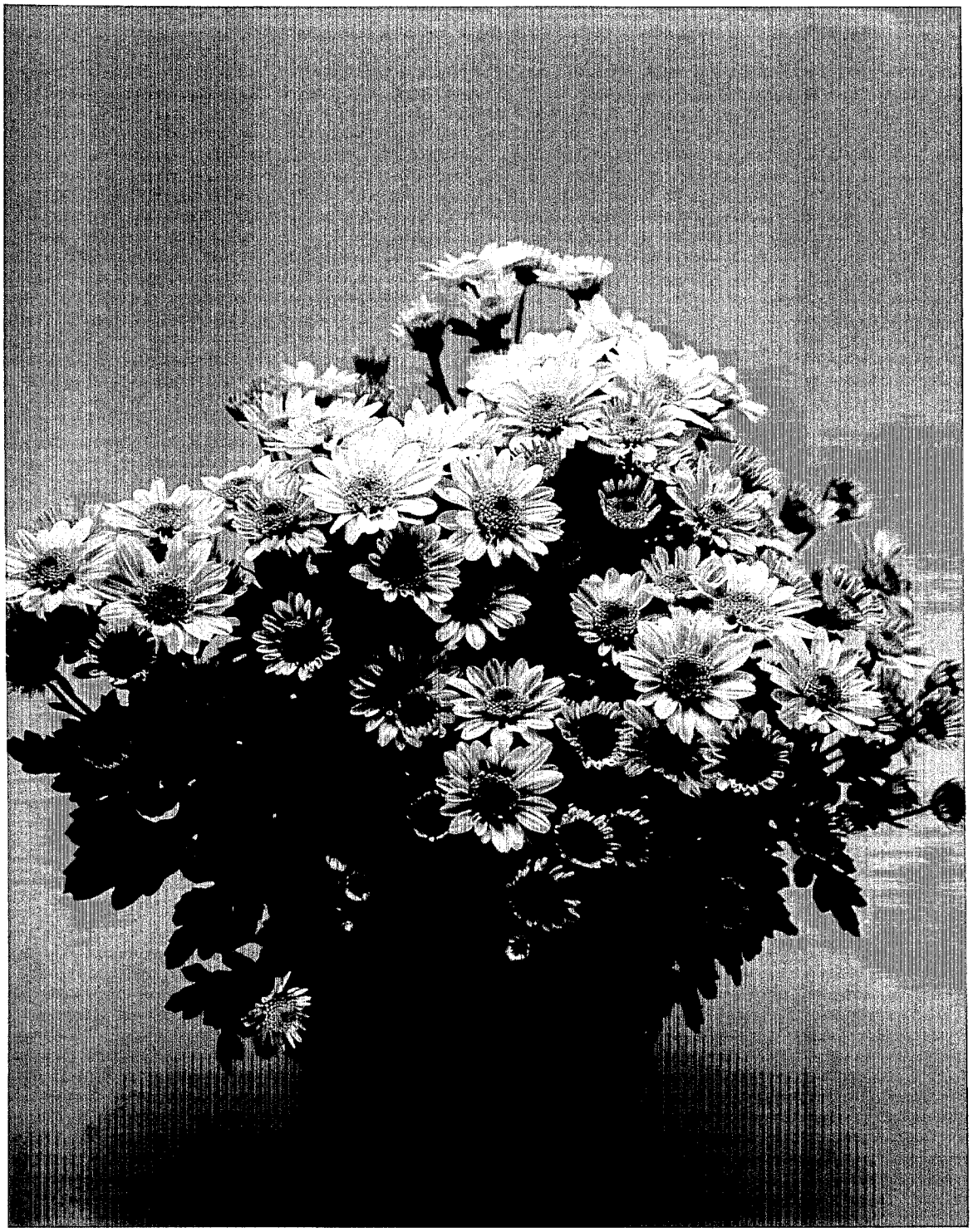

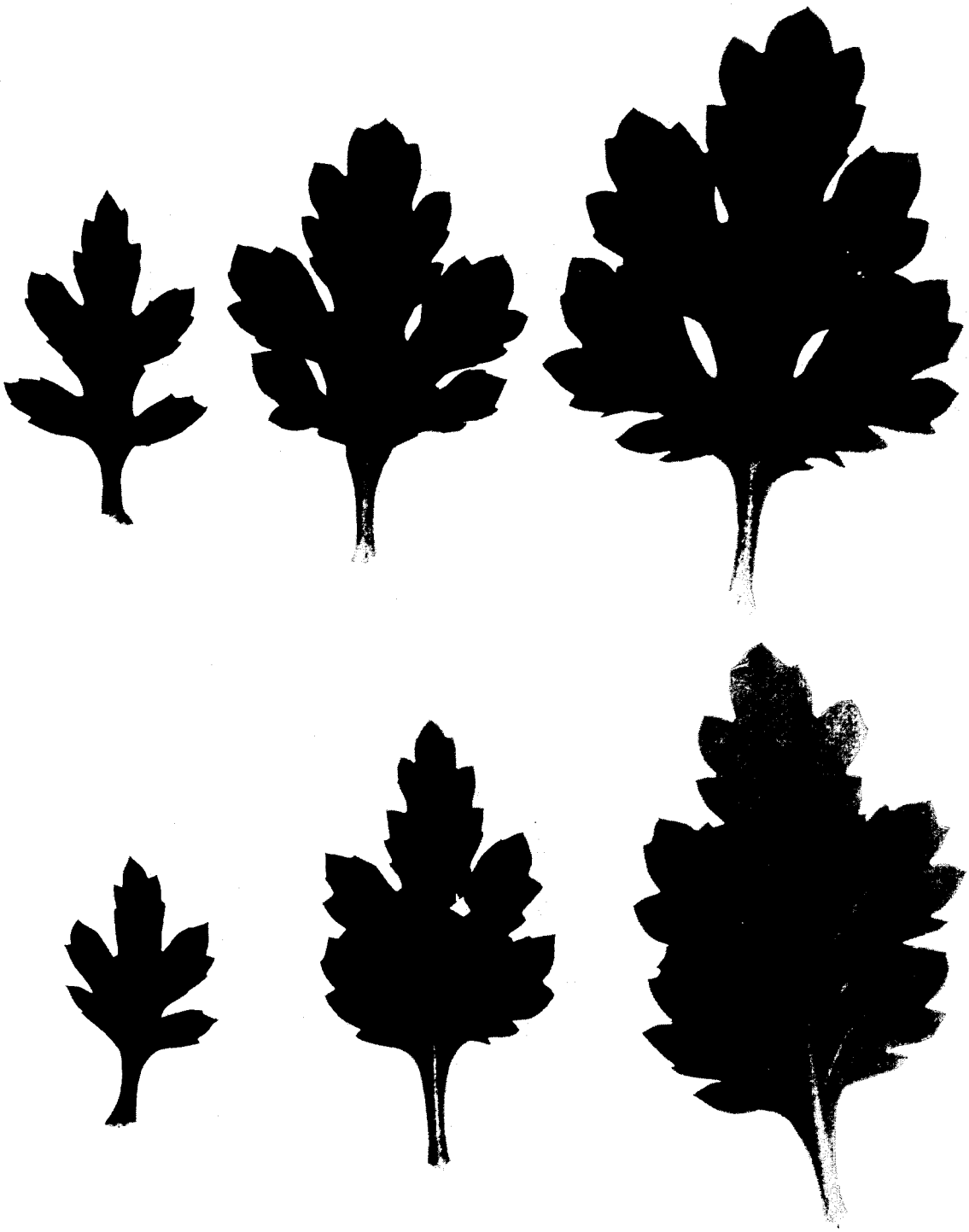

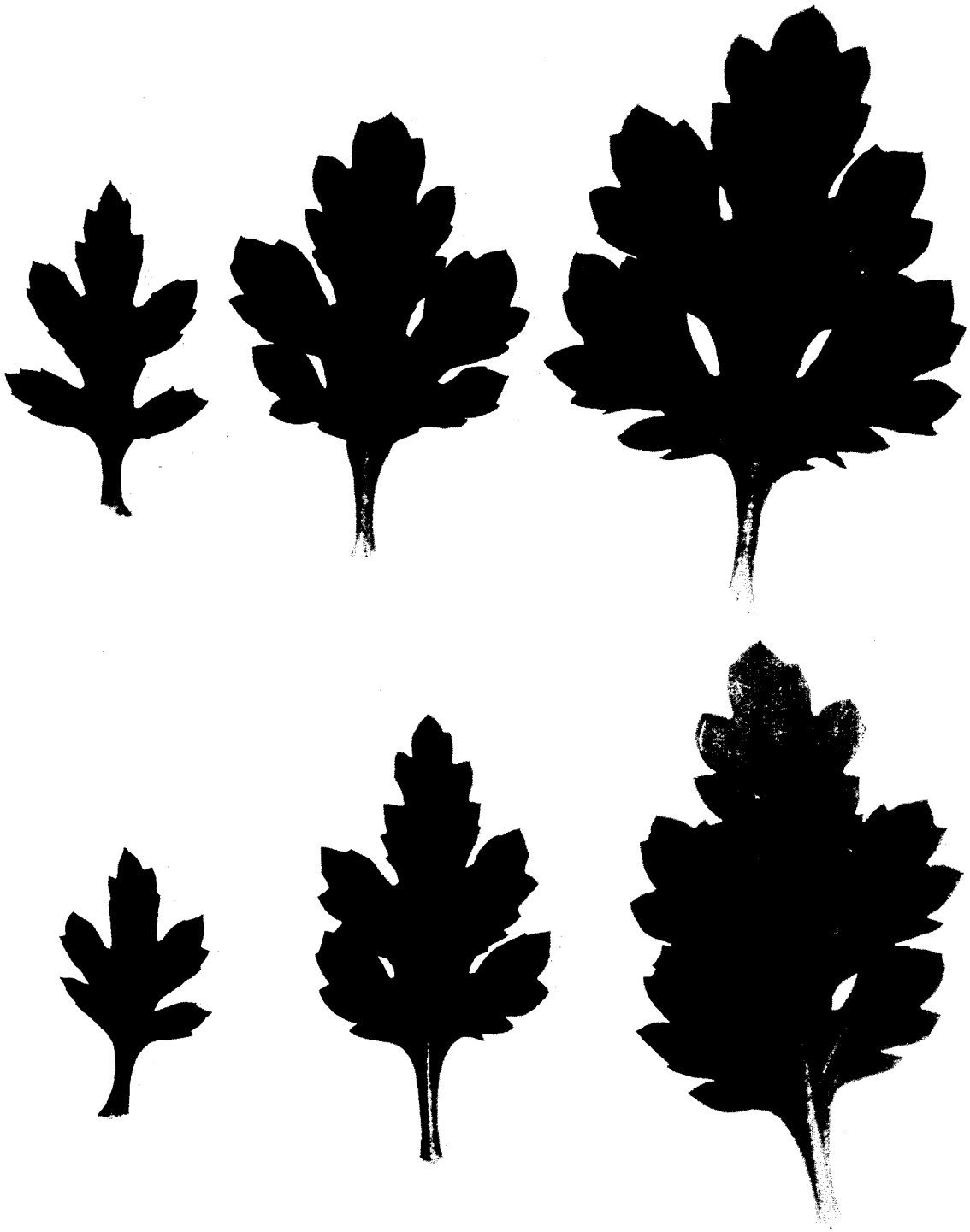

* * * * *